(12) United States Patent
Murray et al.

(10) Patent No.: US 9,144,494 B2
(45) Date of Patent: Sep. 29, 2015

(54) DELIVERY CATHETER SYSTEM WITH MICRO AND MACRO MOVEMENT CONTROL

(75) Inventors: Robert Murray, Santa Rosa, CA (US); Sameer Upadhyaya, Santa Rosa, CA (US); Mark Casley, Galway (IE); Patrick MacAulay, Windsor, CA (US); Ak Masud, Maple Grove, MN (US); Paul Cassidy, Shoreview, MN (US); David Clarke, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 743 days.

(21) Appl. No.: 13/469,670

(22) Filed: May 11, 2012

(65) Prior Publication Data

US 2012/0310332 A1 Dec. 6, 2012

Related U.S. Application Data

(60) Provisional application No. 61/485,455, filed on May 12, 2011, provisional application No. 61/485,434, filed on May 12, 2011.

(51) Int. Cl.
*A61F 2/24* (2006.01)
*A61F 2/966* (2013.01)
*A61F 2/00* (2006.01)
*A61F 2/95* (2013.01)

(52) U.S. Cl.
CPC .............. *A61F 2/2436* (2013.01); *A61F 2/966* (2013.01); *A61F 2/0095* (2013.01); *A61F 2/95* (2013.01); *A61F 2002/9517* (2013.01)

(58) Field of Classification Search
CPC ......... A61F 2/2436; A61F 2/966; A61F 2/95; A61F 2/962; A61F 2/2427
USPC ............... 623/1.11, 1.12, 1.23, 2.11; 606/108
See application file for complete search history.

(56) References Cited

U.S. PATENT DOCUMENTS

| | | |
|---|---|---|
| 2005/0027305 A1 | 2/2005 | Shiu et al. |
| 2010/0049313 A1 | 2/2010 | Alon et al. |
| 2011/0282425 A1* | 11/2011 | Dwork .......................... 623/1.11 |

FOREIGN PATENT DOCUMENTS

| | | |
|---|---|---|
| EP | 1 731 189 A1 | 12/2006 |
| EP | 1 982 677 A2 | 10/2008 |
| WO | WO 2009/140971 A1 | 11/2009 |
| WO | WO 2011/011023 A1 | 1/2011 |

* cited by examiner

*Primary Examiner* — Jonathan W Miles

(57) ABSTRACT

A prosthetic valve delivery system that is improved in controllability by way of a proximal handle system. Such a handle system of the present invention advantageously permits a controlled fine or micro movement or adjustment of a distal sheath for uncovering a plunger that is to be loaded with a prosthetic valve for deployment thereof. The delivery system of the present invention permits a trigger-release for a gross or macro movement to the sheath relative to the plunger. Also, the control handle of the delivery system is shaped and contoured for ease in manipulation of the micro-control actuator.

24 Claims, 13 Drawing Sheets

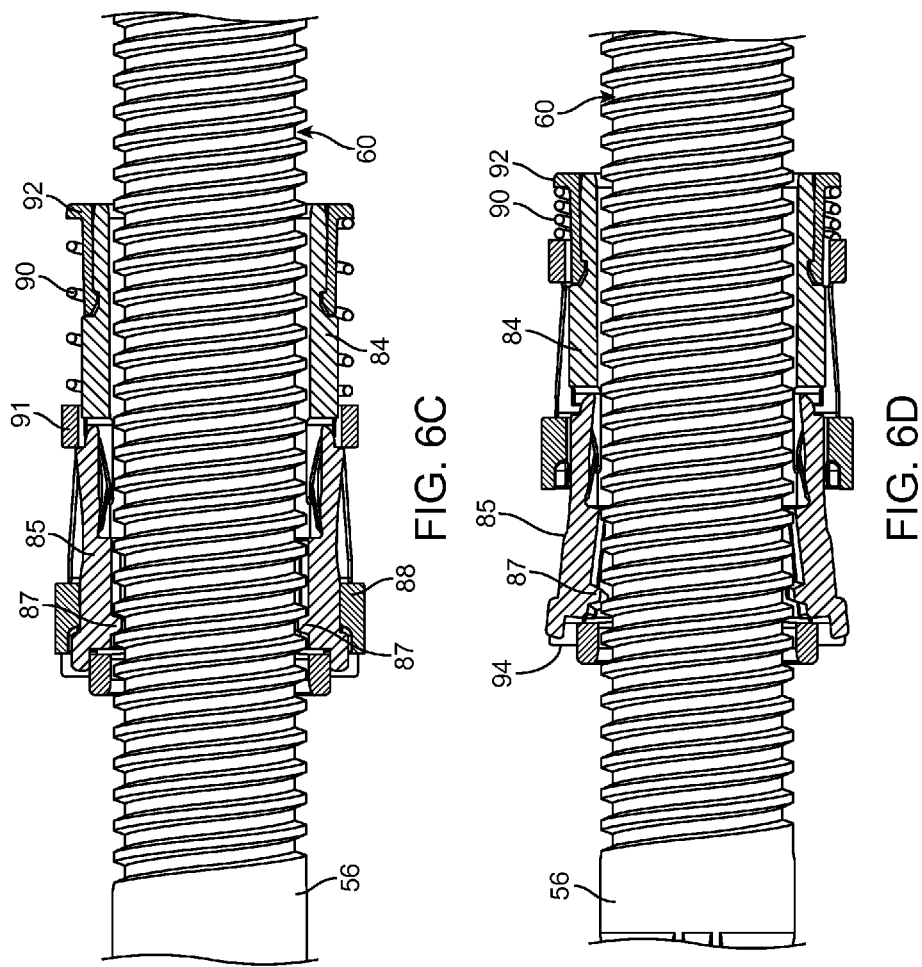

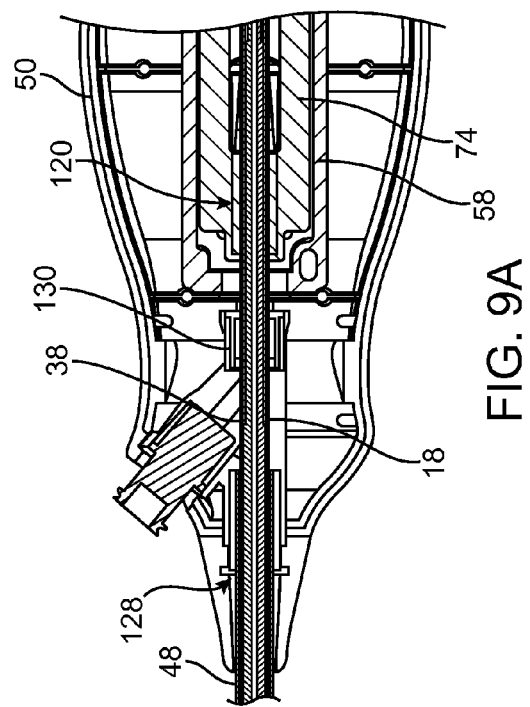
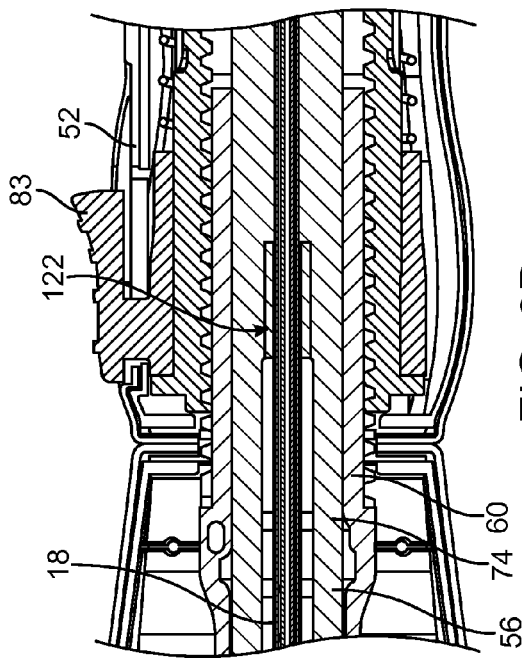
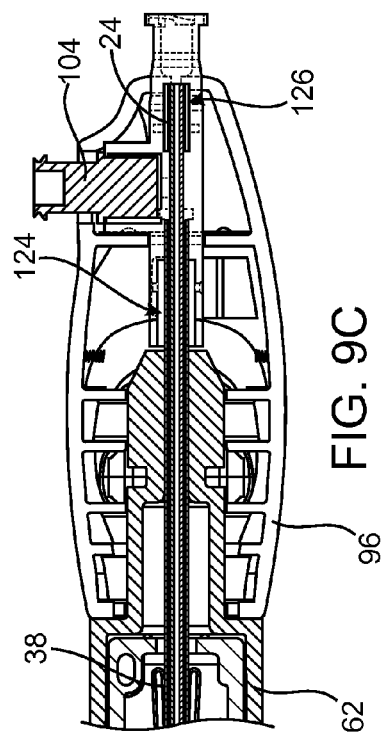

DELIVERY CATHETER SYSTEM WITH MICRO AND MACRO MOVEMENT CONTROL

TECHNICAL FIELD OF THE PRESENT INVENTION

The present invention relates to a delivery system for positioning and deploying a prosthetic heart valve, in particular an aortic heart valve. More specifically, the present invention is directed to aspects of providing the delivery system for use by a surgeon and of controlling the delivery and deployment of such a prosthetic heart valve.

BACKGROUND OF THE PRESENT INVENTION

Recently, there has been interest in minimally invasive and percutaneous replacement of cardiac valves. In the specific context of pulmonary valve replacement, for example, U.S. Patent Application Publication Nos. 2003/0199971 A1 and 2003/0199963 A1, both filed by Tower, et al. and incorporated herein by reference, describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the native valve leaflets against the right ventricular outflow tract, thereby anchoring and sealing the replacement valve.

As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, both incorporated herein by reference in their entireties, the replacement pulmonary valve may be implanted to replace native pulmonary valves or prosthetic pulmonary valves located in valved conduits. Other articles that describe features of percutaneous valve implantation include Louise Coats, et al., "The Potential Impact of Percutaneous Pulmonary Valve Stent Implantation on Right Ventricular Outflow Tract Re-Intervention," European Journal of Cardio-Thoracic Surgery (England), April 2005, pgs. 536-43; Peter C. Block, et al., "Percutaneous Approaches to Valvular Heard Disease," Current Cardiology Reports (United States), March 2005, pgs. 108-13; Georg Lutter, et al., "Percutaneous Valve Replacement: Current State and Future Prospects," Annals of Thoracic Surgery (Netherlands), December 2004, pgs. 2199-206; Younes Boudjemline, et al., "Percutaneous Pulmonary Valve Replacement in a Large Right Ventricular Outflow Tract: An Experimental Study," Journal of the American College of Cardiology (United States), Mar. 17, 2004, pgs. 1082-7; S. Khambadkone, et al., "Percutaneous Implantation of Pulmonary Valves," Expert Review of Cardiovascular Therapy (England), November 2003, pgs. 541-18; Y. Boudjemline, et al., "Percutaneous Valve Insertion: A New Approach," Journal of Thoracic and Cardiovascular Surgery (United States), March 2003, pgs. 741-2; Philipp Bonhoeffer, et al., "Percutaneous Insertion of the Pulmonary Valve," Journal of the American College of Cardiology (United States), May 15, 2002, pgs. 1664-9; Younes Boudjemline, et al., "Steps Toward Percutaneous Aortic Valve Replacement," Circulation (United States), Feb. 12, 2002, pgs. 775-8; P. Bonhoeffer, et al., "Percutaneous Replacement of Pulmonary Valve in a Right-Ventricle to Pulmonary-Artery Prosthetic Conduit with Valve Dysfunction," Lancet (England), Oct. 21, 2000, pgs 1403-5; P. Bonhoeffer, et al., "Transcatheter Implantation of a Bovine Valve in Pulmonary Position: A Lamb Study," Circulation (United States), Aug. 15, 2000, pgs. 813-6; G. O. Yonga et al., "Effect of Percutaneous Balloon Mitral Valvotomy on Pulmonary Venous Flow in Severe Mitral Stenosis," East African Medical Journal (Kenya), January 1999, pgs. 28-30; and G. O. Yonga, et al., "Percutaneous Transluminal Balloon Valvuloplasty for Pulmonary Valve Stenosis: Report on Six Cases," East African Medical Journal (Kenya), April 1994, pgs. 232-5, all of which are also incorporated herein by reference in their entireties.

The approach to pulmonary valve replacement described in the above patent applications and articles remains a viable treatment for certain patients. In particular, the Melody valve is a commercial form of a pulmonary valve replacement available from Medtronic, Inc. that is usable according to the above noted approach. Other techniques have also been developed to broaden those patients that can benefit from such pulmonary valve replacement procedures including the provision of other size valves than those of sizes that can be created from the size range of available valved segments of bovine jugular veins.

A delivery system that is associated with the Melody pulmonary valve is also commercially available from Medtronic, Inc. The Melody delivery system is a catheter system that includes an inflatable balloon at a distal end of the device onto which the pulmonary valve replacement is crimped. This system is designed for control and steerability from a proximal end of the device for guiding the pulmonary valve replacement to position within a patient's heart via the patient's vasculature. In particular, this system is designed for deployment by the balloon at the patient's native pulmonary valve annulus as accessed via the femoral vein of the patient. The valve is typically sheathed as crimped directly onto the distal balloon of the delivery system and includes the ability to slide the sheath from covering the collapsed replacement valve so that the balloon can thereafter be expanded for permanently deforming and expanding the metal structure of the replacement valve into a permanent position at the pulmonary valve annulus.

Percutaneous aortic valve replacement procedures are also being investigated. One such valve that has been successfully deployed from a catheter delivery system is the CoreValve aortic valve and system, that is also available from Medtronic, Inc. The CoreValve aortic valve replaces the aortic valve in patients with severe aortic stenosis. The valve leaflets are provided by utilizing a porcine pericardial valve that is sutured to the expandable metal frame. This expandable metal frame, however, utilizes Nitinol metal allow so that the frame and thus the aortic valve is self-expanding for controlled deployment at the aortic valve annulus. This frame structure is typically around 5 cm long and is shaped along its length with a non-uniform diameter for improved anchoring of the aortic valve in position at the valve annulus. Further disclosure of aspects of the CoreValve aortic valve and delivery system are provided within U.S. Pat. Nos. 7,682,390, 7,780,726 and 7,892,281.

Delivery of the CoreValve aortic valve prosthesis or any other percutaneous and self-expandable aortic valve prosthesis typically requires a movable sheath at the distal end of a delivery system that maintains a compressed valve prosthesis beneath the sheath. Retraction of the sheath in a proximal direction of the delivery system as controlled from the proximal end of the delivery system is controlled for deploying the self-expandable valve prosthesis from one end thereof to another. Specifically, a distally positioned end of the valve prosthesis initially expands as the sheath is retracted while a proximally positioned end of the valve prosthesis remains collapsed within the confines of the sheath. A gradual expansion is thus controlled so that the full prosthetic valve is deployed in position, such as at a particular valve annulus. Typically, controlled expansion is conducted by maintaining the prosthetic valve as positioned on the distal end of the delivery system at a precise position, such as determined by fluoroscopy, while sliding the sheath proximally relative to the prosthetic valve and distal end of the delivery system. Self-expansion of the valve prosthesis deploys the prosthesis in this precise position and expansion of the metal frame of the prosthetic valve anchors the prosthetic valve in place. The sliding movement of the sheath can be conducted manually by a surgeon, for example, and such movement can be facilitated and controlled by mechanical means incorporated within a handle at the proximal end of the delivery system.

One such delivery system that has been designed for delivery of a self-expanding valve prosthesis is the AccuTrak™ delivery system that is commercially available from Medtronic, Inc. and is provided as a part of a system including the CoreValve aortic valve prosthesis, discussed above. The Accutrak delivery catheter system is a single use, intravascular "over the wire" delivery catheter designed specifically to be used with the Medtronic CoreValve percutaneous aortic valve. The Accutrak system incorporates a protective deployment sheath that houses and deploys the aortic valve prosthesis. The Accutrak system includes an integrated handle designed to provide the user with accurate and controlled deployment. After the deployment system is placed in the vicinity of the aortic annulus, the user retracts the deployment sheath, thereby deploying the prosthetic aortic valve to the desired location. The system includes a micro-control thumb wheel and a macro-control slide, each of which are independently provided to the control handle thereof. In use, the deployment sheath can be partially pulled back to evaluate the PAV location prior to fully releasing the PAV. In this way, the user can make slight adjustments to the PAV location if needed prior to release.

SUMMARY OF THE PRESENT INVENTION

The present invention overcomes shortcomings and deficiencies of prior art delivery systems by providing a prosthetic valve delivery system that is improved in controllability by way of a proximal handle system. Such a handle system of the present invention advantageously permits a controlled fine or micro movement of a distal sheath for uncovering a prosthetic valve for deployment thereof, and also permits a quick-release for a gross or macro movement to the sheath.

In one aspect of the present invention, a delivery system is provided for percutaneous delivery of an expandable prosthetic heart valve, as such a prosthetic heart valve is to be collapsed and loaded onto a distal deployment portion of the delivery system. Such a delivery system includes:

an elongate catheter portion that extends from a proximal end to a distal end and that includes a first shaft with an axial lumen and a second shaft within the lumen of the first shaft;

a deployment portion at a distal end of the delivery system that is operatively connected with the catheter portion and comprises a plunger attached to the second shaft of the catheter portion and a sheath connected with the first shaft of the catheter portion, wherein relative movement between the first and second shafts also provides relative movement of the plunger and sheath so that a valve supporting portion of the plunger can be effectively covered and uncovered by the sheath; and a control handle portion at a proximal end of the delivery system and comprising a micro-control actuator that is operatively connected to the first shaft and is provided to advance and retract along a screw shaft that is operatively connected with the second shaft so that translation of the micro-control actuator along the screw shaft by rotation of the micro-control actuator translates the sheath relative to the plunger in a controlled micro-adjustment manner, wherein the micro-control actuator is also releasable from the screw shaft so that the micro-control actuator can be translated along the screw shaft without rotation of the micro-control actuator in a controlled macro-adjustment manner.

In accordance with another aspect of the present invention, a delivery system is provided for percutaneous delivery of an expandable prosthetic heart valve, as such a prosthetic heart valve is to be collapsed and loaded onto a distal deployment portion of the delivery system, wherein the delivery system includes:

an elongate catheter portion that extends from a proximal end to a distal end and that includes a first shaft with an axial lumen and a second shaft within the lumen of the outer shaft;

a deployment portion at a distal end of the delivery system that is operatively connected with catheter portion and comprises a plunger attached to the second shaft of the catheter portion and a sheath connected with the first shaft of the catheter portion, wherein relative movement between the first and second shafts also provides relative movement of the plunger and sheath so that a valve supporting portion of the plunger can be effectively covered and uncovered by the sheath; and a control handle portion at a proximal end of the delivery system and comprising a micro-control actuator that is operatively connected to the sheath for moving the sheath relative to the plunger by rotation of the micro-control actuator in a controlled micro-adjustment manner, wherein the micro-control actuator is also includes a releasable trigger for permitting linear movement of the micro-control actuator and thus movement of the sheath without rotation of the micro-control actuator in a controlled macro-adjustment manner.

In accordance with yet another aspect of the present invention, a delivery system is provided for percutaneous delivery of an expandable prosthetic heart valve, as such a prosthetic heart valve is to be collapsed and loaded onto a distal deployment portion of the delivery system, wherein the delivery system includes:

an elongate catheter portion that extends from a proximal end to a distal end and that includes a first shaft with an axial lumen and a second shaft within the lumen of the outer shaft;

a deployment portion at a distal end of the delivery system that is operatively connected with catheter portion and comprises a plunger attached to the second shaft of the catheter portion and a sheath connected with the first shaft of the catheter portion, wherein relative movement between the first and second shafts also provides relative movement of the plunger and sheath so that a valve supporting portion of the plunger can be effectively covered and uncovered by the sheath; and a control handle portion at a proximal end of the delivery system and comprising a micro-control actuator that is operatively connected to the sheath for moving the sheath relative to the plunger by rotation of the micro-control actuator in a controlled micro-adjustment manner, wherein a front grip is positioned distally adjacent to the micro-control actuator and a carriage is positioned proximally adjacent to the micro-control actuator, and further wherein the front grip, the micro-control actuator, and the carriage are positionable in a linear arrangement next to one another and defining a smooth contoured side profile with at least the front grip and the micro-control actuator including surface curvatures providing at least an outward bulge to the front grip and an inward curve to the micro-control actuator.

BRIEF DESCRIPTION OF THE DRAWINGS

FIG. 6C is a view similar to FIG. 6B with the threaded insert assembly in cross-section and illustrating a micro-control position thereof;

FIG. 6D is a view similar to FIG. 6C with the threaded insert assembly in cross-section and illustrating a macro-control position thereof;

FIG. 9A is an enlarged cross-sectional view of a distal portion of the handle assembly including a distal portion of the front grip and of the internal screw shaft;

FIG. 9B is an enlarged cross-sectional view of an intermediate portion of the handle assembly including intermediate portions of the front grip and of the micro-control actuator;

FIG. 9C is an enlarged cross-sectional view of a proximal portion of the handle assembly including a proximal portion of the internal screw shaft and of the tip retractor;

DETAILED DESCRIPTION OF THE PREFERRED EMBODIMENTS

Figure 1:
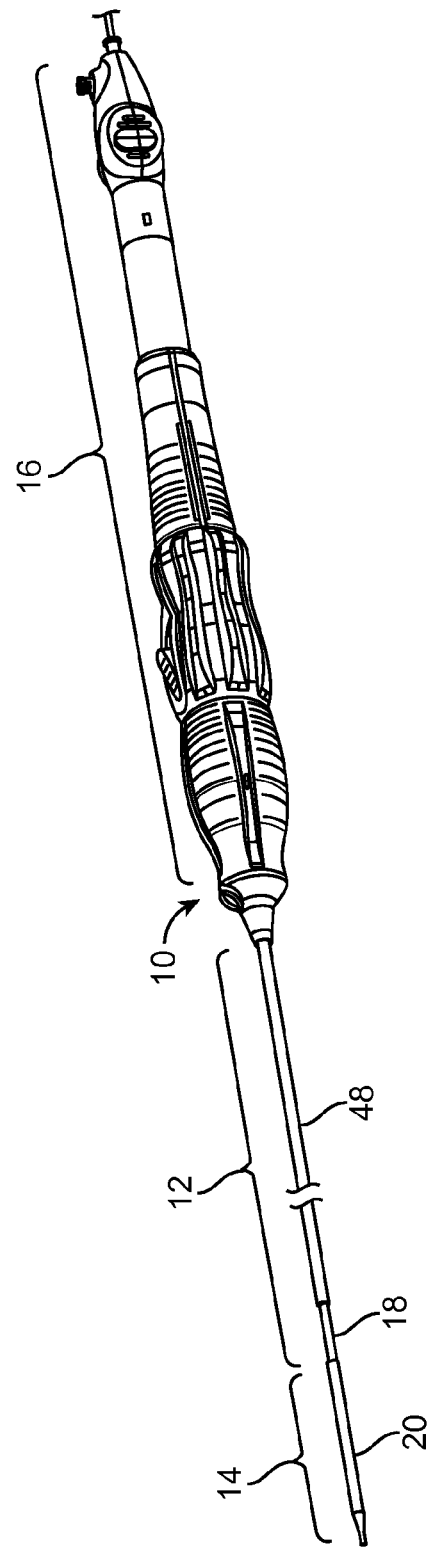
FIG. 1 is a perspective view of a delivery system in accordance with the present invention including a control handle assembly that is provided at a proximal end of the delivery system for selectively controlling movement of a prosthesis covering sheath at a distal end of the delivery system, which handle assembly controls both micro movement and a quick-release macro movement of the sheath, along with releasable components of the delivery system in order to facilitate quicker and easier delivery, system withdraw, and deployment of a prosthetic heart valve.

Referring now to the Figures, wherein the components are labelled with like numerals throughout the several Figures, and initially to FIG. 1, an exemplary delivery system 10 is illustrated for percutaneous insertion and implantation of a biological valvular replacement to a desired implant location, such as within a patient's heart. A prosthetic heart valve can be delivered by delivery systems of the present invention as such prosthetic heart valves can be designed for replacement of the aortic valve, mitral valve, tricuspid valve, or pulmonary valve by way of a patient's vasculature, such as including access through a patient's femoral artery or femoral vein, or otherwise, as appropriate in accordance with known or developed delivery techniques utilizing percutaneous delivery. Delivery systems according to the present invention improve the ease and accuracy of prosthetic valve delivery through the vasculature and avoid deployment difficulties related to the need to control the delivery and deployment actions at the distal end of such a delivery system from a proximally provided control handle.

Delivery system 10 is preferably used for delivering an expandable metal frame valve to a desired implant location, such as by way of, the femoral artery, the femoral vein, the pulmonary vein, a valved conduit, or otherwise. One preferably expandable valve that is desired to be delivered by the delivery system 10 of the present invention is the CoreValve aortic valve, as is commercially available from Medtronic, Inc., the assignee of the present invention, and as certain aspects thereof are described within U.S. Pat. Nos. 7,682,390, 7,780,726 and 7,892,281, the entire disclosures of which are incorporated herein by reference.

As shown in FIG. 1, delivery system 10 generally comprises a catheter portion 12, a distal deployment portion 14, and a proximal control handle portion 16 by which the deployment portion 14 is effectively controlled. The catheter portion 12 is preferably of a length and size so as to permit a controlled delivery of the deployment portion 14 to a desired implant location of a patient's heart, for example. Preferably, the catheter portion 12 includes features to enhance manoeuvrability, steerability and advancement of the deployment portion 14 to the point of implantation, as further discussed below. The deployment portion 14 provides the means by which a metal frame prosthetic valve can be mounted for delivery to the implantation location and further provides for allowing the expansion of the metal frame prosthetic valve for effective deployment thereof. The control handle portion 16 preferably controls movements as translated to the deployment portion 14 by way of elongate structure of the catheter portion 12. Controlled functionality from the control handle portion 16 is preferably provided in order to permit expansion and deployment of a metal frame prosthetic valve at a desired location, such as a heart valve annulus, and to provide for ease in the delivery and withdrawal of the delivery system through a patient's vasculature.

The catheter portion 12 comprises plural elongate elements preferably including a flexible outer shaft 18 that is operatively connected with the control handle portion 16 so as to be movable by operation of the handle control portion, as described below, and that is connected with a sheath 20. Movement of the sheath 20 proximally from its distal-most position exposes a plunger 22 that is connected with an inner shaft 24. The inner shaft 24 is also operatively connected with the control handle portion 16, but so as to be relatively fixed with respect to the outer shaft 18 and sheath 20. That way, relative movement of the outer shaft 18 and sheath 20 with respect to the plunger 22 and inner shaft 24 provides for a controlled covering or exposing of the plunger 22. More particularly, when an expandable prosthetic heart valve is collapsed onto the plunger 22, withdrawing of the sheath 20 to expose the prosthetic valve as collapsed onto the plunger 22 provides for controlled expansion of the prosthetic valve and controlled deployment thereof. Where the prosthetic valve comprises a metal frame valve that is self expanding, the proximal movement of the sheath 20 allows the metal frame of the valve to expand for deployment of its valve leaflets in position as located by delivery system 10.

Figure 4:
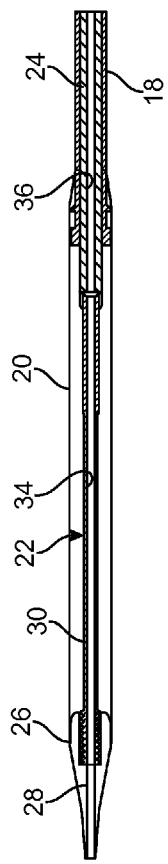
FIG. 4 is an enlarged cross-sectional view of the plunger and sheath portion of the delivery system of the delivery system of FIG. 3.

With reference to FIG. 4, in particular, the sheath 20 is illustrated at a distalmost or closed position with a leading edge thereof abutting against a perimetric shoulder 26 of a nosecone 28 that is provided as the leading feature of the plunger 22. Proximally from the nosecone 28, the plunger 22 comprises a reduced diameter portion 30 onto which an expandable prosthetic heart valve is to be collapsed. At the proximal-most end of the plunger 22, a increased diameter portion 32 defines a proximal edge for positioning the collapsed valve distally and also provides a connection point for connecting the plunger 22 to the distal end of the inner shaft 24. A lumen 34 passing axially through the plunger 22 also preferably aligns with a lumen 36 of the inner shaft 24 as these components are fixed together to provide a continuous lumen.

A flush tube 38 is provided that preferably extends over a proximal portion of the inner shaft 24, the purpose and connection of the flush tube 38 with the inner shaft 24 described in greater detail below. The inner shaft 24 also preferably includes an axial lumen extending entirely though it, the purpose of which is for receiving a guide wire, as well known, in order for the delivery system 10 to be guided along a patient's vasculature to an implant location. The guide wire, not shown, may be, for example, a 0.089 cm extra stiff guidewire as manufactured by Amplatzer of Golden Valley, Minn., and be used in a conventional manner to guide the delivery system along it and with its distal end guided to its desired implant location.

The catheter portion 12 of the delivery system 10 also preferably comprises a stability shaft 48 that is also operatively connected with a distal end of the control handle portion 16 and that surrounds the outer shaft 18 over at least a part of its length. Preferably, the stability shaft 48 comprises a lubricous inner layer (such as high density polyethylene HDPE or Polytetrafluoroethylene PTFE), braided stainless steel middle layer with a flexible plastic outer layer, such as comprised of Pebax 7233, or Nylon 12. Preferably, the stability shaft 48 extends to approximately 80% of the length of the catheter portion 12 of the delivery system as such extends from the control handle portion 16. Such a stability layer 48 facilitates the advancement and steering of the delivery system along a guide wire and through a patient's vasculature by improving the pushability of the delivery system 10. Also, the additional stability shaft 48 adds some stiffness to the proximal end of the catheter portion 12 which translates into a more supportive structure for the catheter portion. This stiffness of stability shaft will minimize the movement of the catheter portion within the anatomy during the deployment of a prosthetic valve. This feature aids the user in making a more accurate deployment because of less movement of the catheter portion within the anatomy during deployment.

Figure 2:
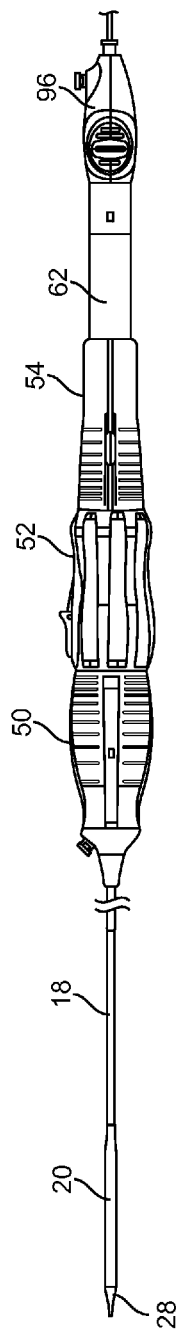
FIG. 2 is a side view of the delivery system of FIG. 1 illustrating a front grip portion, a translating rotator portion including a quick-release button, a proximal hand rest portion, and a tip retractor portion.
Figure 3:
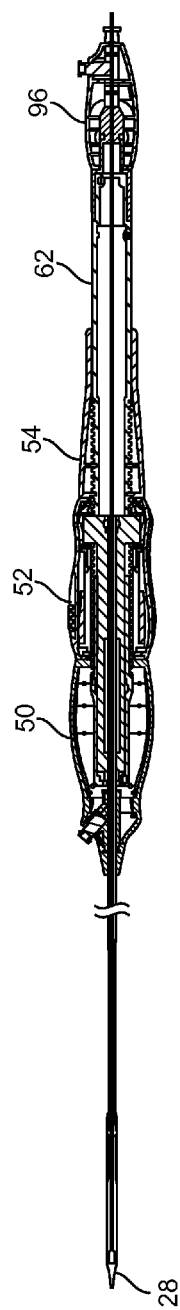
FIG. 3 is a cross-sectional view of the delivery system of FIG. 2 illustrating an internal screw shaft that is fixed with a plunger at a distal end of the delivery system by an inner tube and that is relatively movable to an outer tube that is connected with a sheath at the distal end of the delivery system so that the translating rotator moves along the internal screw shaft to move the sheath relative to the plunger as the plunger is maintained at a desired deployment position.

The control handle portion 16 is designed, among other things, for controlling the covering and the withdrawal of the sheath 20 with respect to the plunger 22, and further with respect to an expandable prosthetic heart valve as such can be collapsed onto the plunger 22, as described above. With reference to FIGS. 2 and 3, in particular, the control handle portion 16 comprises a front grip 50, a micro-control actuator 52, and a carriage 54 as those elements that are grasped and manipulated by a surgeon during a procedure according to the present invention for controlling the covering and withdrawing of the sheath 20 relative to the plunger 22. This functionality is achieved by a relative movement between the front grip 50 and the micro-control actuator 52, as the micro-control actuator 52 is operatively connected with the outer shaft 18. Specifically, the micro-control actuator 52 and the carriage 54 can translate together along a screw shaft 56 that is fixed with the front grip 50.

Figure 6A:
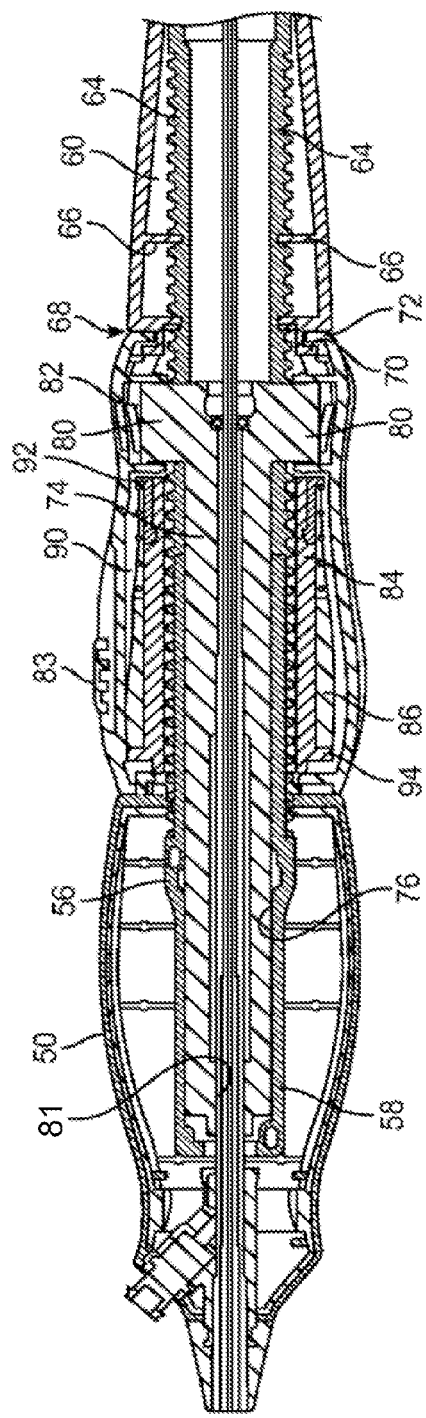
FIG. 6A is an enlarged cross-sectional view of an assembly including the internal screw shaft along with a drive tube that is internal to the screw shaft, as such assembly is positioned within the front grip, translating rotor and proximal hand rest.
Figure 7:
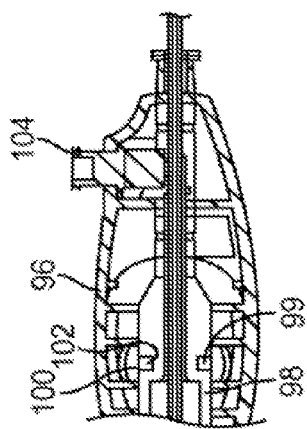
FIG. 7 is an enlarged cross-section of a quickly releasable tip retractor.
Figure 6B:
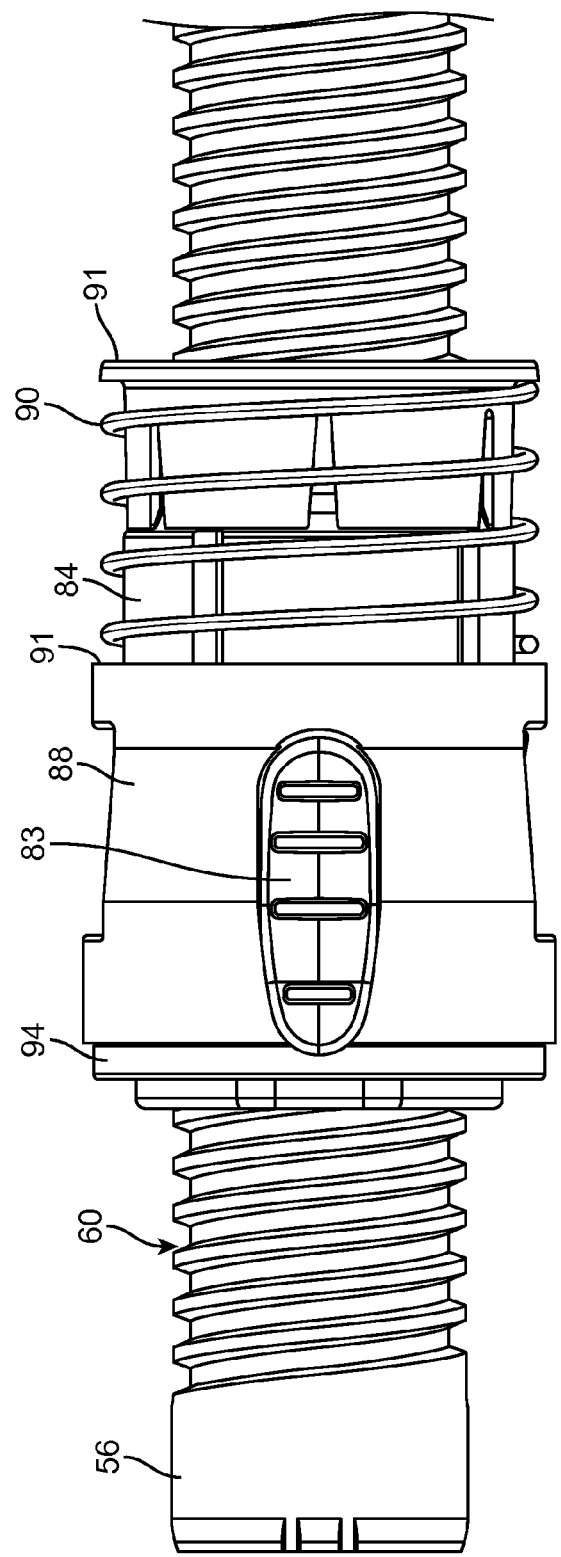
FIG. 6B is a further enlarged view of the internal screw shaft and a threaded insert assembly.
Figure 8:
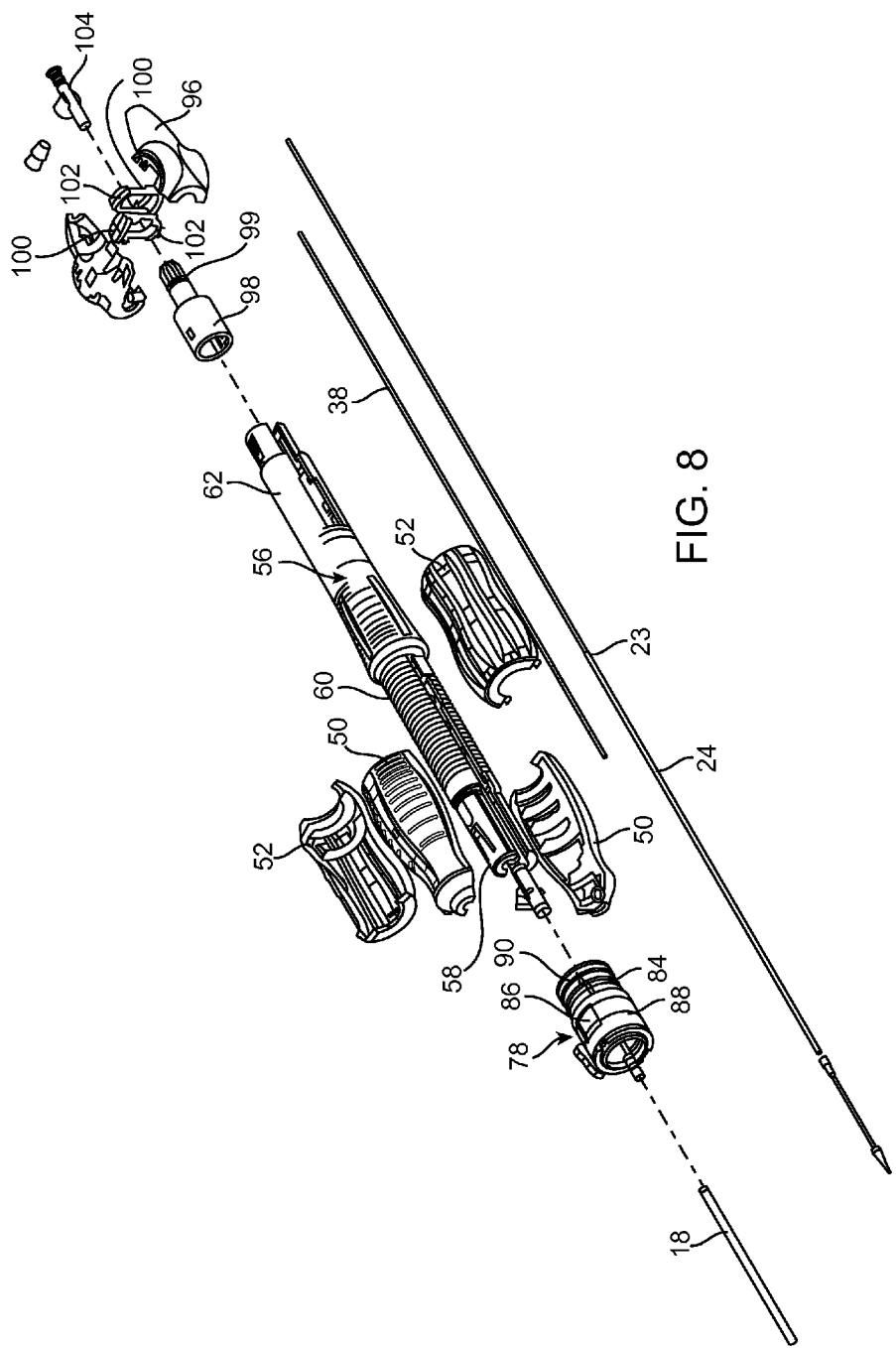
FIG. 8 is a partially exploded view of the delivery system of the previous figures showing the control handle assembly components.

As shown in FIG. 6A and FIG. 9A, the screw shaft 56 includes a distal portion 58 that fits within and is fixed to the front grip 50. More proximally, the screw shaft increases in diameter to an elongate threaded portion 60 that extends at least through the axial distance of the micro-control actuator 52. Proximally of the threaded portion 60, a non-threaded portion 62 extends along which the carriage 54 can translate. The micro-control actuator 52 preferably translates along the screw shaft 56 by rotation thereof in the manner of a nut moving along a threaded shaft. The carriage 54 is preferably axially movable along the screw shaft 56 without rotating as the carriage 54 is pushed or driven by the micro-control actuator 52 so that they are together translated along the screw shaft. As illustrated, the screw shaft 56 preferably includes a pair of diametrically opposed slots 64 that extend over a proximal portion of the threaded portion 60 of the screw shaft. Pins 66 are provided inward from the carriage 54 and to extend into the slots 64. This arrangement allows the carriage 54 to translate along the screw shaft 56 without rotating. The carriage 54 is also preferably axially connected to the micro-control actuator 52 such as shown at 68, whereby an inner annular flange 70 of the carriage 56 fits within an outer annular flange 72 of the micro-control actuator 52. This arrangement allows the micro-control actuator 52 to rotate relative to the carriage 56, but connects them in order to be axially movable together.

Figure 5:
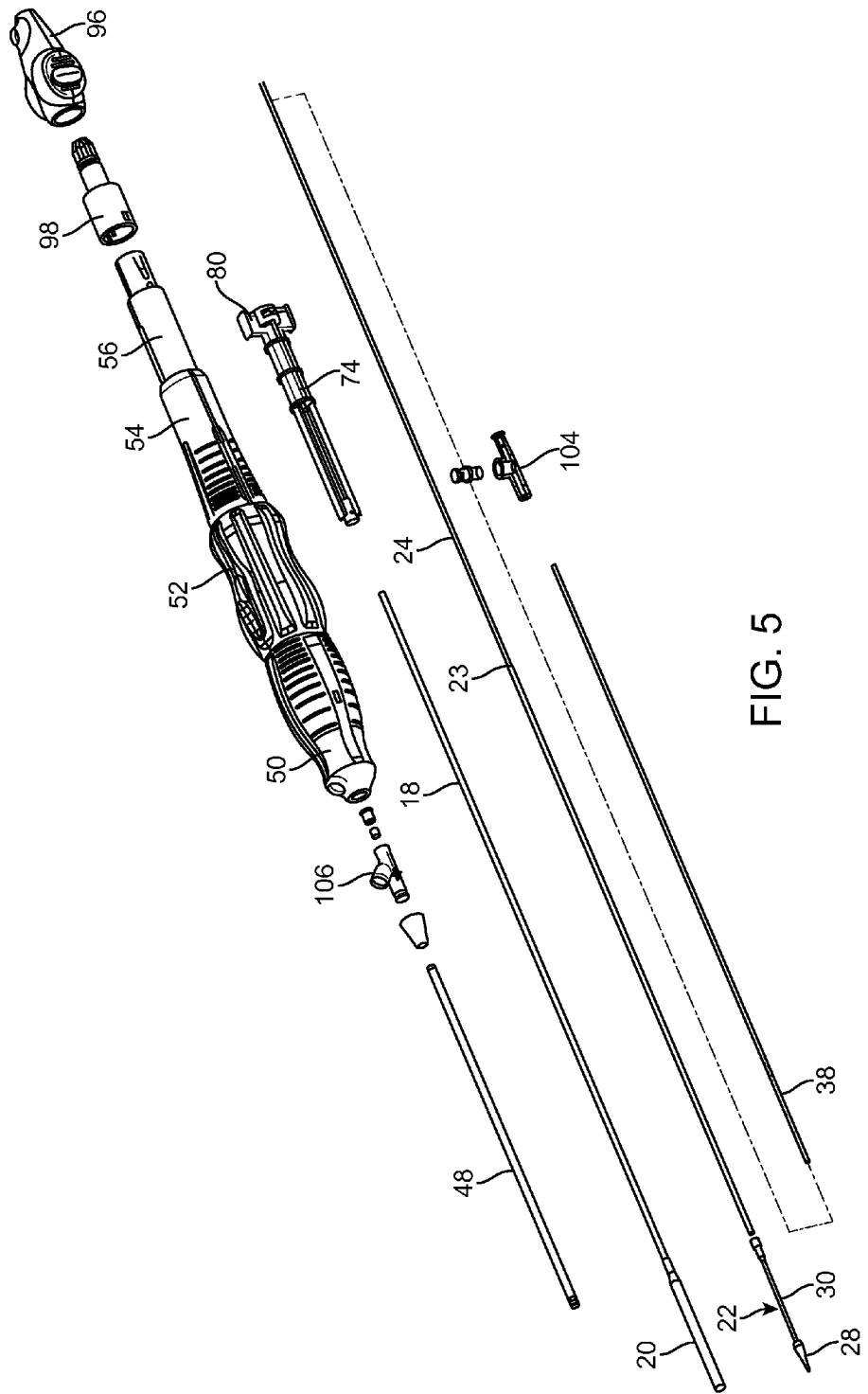
FIG. 5 is a partially exploded view of the delivery system of FIGS. 1-4 illustrating the manner of assembly of an inner shaft relative to an outer shaft and with respect to a stabilizing shaft and a flush tube.

In order to functionally connect the outer shaft 18 so as to translate with the micro-control actuator 52, a T-shaft 74 is movably provided within an internal axial passage 76 of the screw shaft 56. The slots 64 also are open into the internal axial passage 76. As also shown in FIG. 5, the T-shaft 74 comprises a rod portion 78 and a pair of tabs 80 that are provided to extent through the slots 64 of the screw shaft 56 and to fit within an annular recess 82 of the internal side of the micro-control actuator 52. Preferably, the tabs 80 fit closely within the annular recess 82 so that there is a direct movement of the T-shaft 74 in the axial direction as the micro-control actuator 52 moves axially along the screw shaft 56 when rotated. This length of the slots 64 define the range of travel of the T-shaft 74 and thus the micro-control actuator 52 along the screw shaft 56. The rotation is not transmitted to the T-shaft 74 as the interaction of the tabs 80 and slots 64 prevent rotation of the T-shaft relative to the screw shaft 56.

The T-shaft 74 is also operatively fixed with the outer shaft 18 for moving the outer shaft and thus the sheath 20 under the control of the micro-control actuator 52. The proximal end of the outer shaft 18 is preferably provided to extend within a lumen 81 of the T-shaft. The outer shaft 18 can be bonded to the lumen 81 of the T-shaft anywhere along contacting surfaces of the length of contact as desired. Preferably, the outer shaft 18 is bonded to the T-shaft at plural spaced locations, such as at locations 120 and 122, as shown in FIGS. 9A and 9B As a result of this arrangement, axial movement of the T-shaft 74 as controlled by the micro-control actuator 52 is directly translated to the outer shaft 18 and thus the sheath 20.

Figure 10:
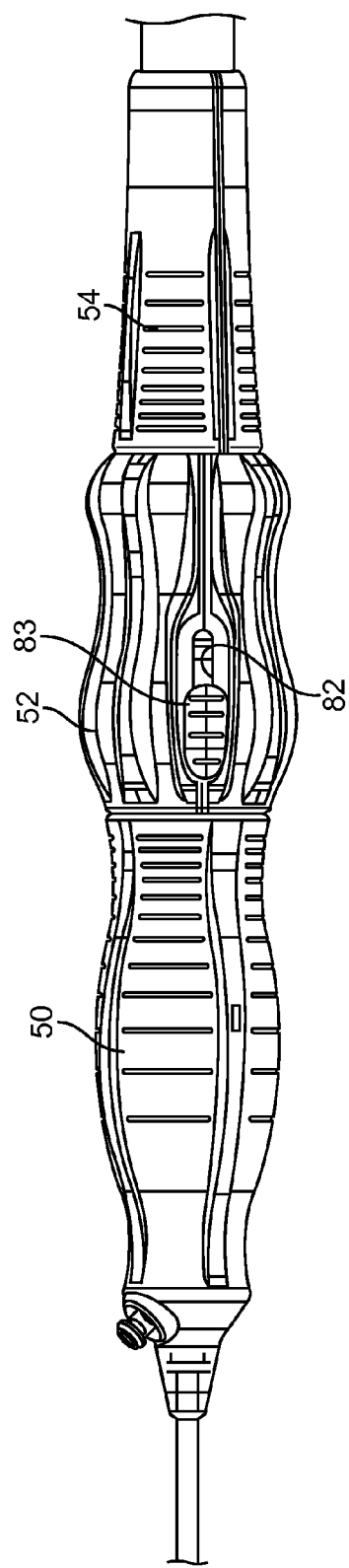
FIG. 10 is a top view of the handle assembly with the quick-release button shown in a locked position along a slide.

In accordance with another aspect of the present invention, the control handle portion 16 includes a macro-actuation ability. Between the micro-control actuator 52 and the screw shaft 56, a threaded insert assembly 78 is provided, as shown in FIGS. 6A, 6B, 6C, 6D and 8, that functions to releasably engage with the threaded portion 60 of the screw shaft 56. Movable female threads of the insert assembly 78 releasably engage with the male threads of the treaded portion 60 so that when they are engaged, rotation of the micro-control actuator 52 causes translation of the micro-control actuator 52 along the screw shaft 56. When released, the micro-control actuator 52 is permitted to freely slide along the screw shaft 56 without rotation along a range of movement that is preferably sufficient to completely cover or uncover the valve support reduced diameter portion 30 of the plunger 22 by the sheath 20. This selective release is preferably controlled by sliding a release trigger 83, as shown also in FIG. 10, which release trigger is preferably movable along a slot 82 of the micro-control actuator 52.

The threaded insert assembly 78, as illustrated, comprises an inner sleeve 84 that rides along the threaded portion 60 of the screw shaft 56 and that includes a pair of diametrically opposed movable tabs 86 that are each provided with a threaded surface 87 to engage with the threads of the threaded portion 60 when the tabs 86 are urged toward the screw shaft 56. The remainder of the inside surface of the inner sleeve 84 is non-threaded to simply slide along the threaded portion 60. The tabs 86 can be formed with the inner sleeve 84 and can be hingedly connected so as to be biased radially outward or away from the threaded portion 60. Alternatively, as shown, the movable tabs 86 can be separately provided elements that fit within slots of the inner sleeve 84 so as to be movable axially along with the inner sleeve 84. Radial constraint can be provided, for example, as described below. Tabs 86 can be provided with shaped outer surfaces 85 that, in effect, cause them to rocker into either a thread engagement position (as shown in FIG. 6C) to a thread non-engagement position (as shown in FIG. 6D) When the tabs 86 are radially moved outward, the threaded portions 87 of the tabs 86 do not threadingly engage with the threaded portion 60, as they are moved or biased outwardly, so that the sleeve 84, and thus the threaded insert assembly 78 can freely move along the screw shaft 56 within the limits by the interaction of the tabs 80 and the slots 64, as described above. It is understood that at least one such threaded portion 87 and movable tab 86 is needed for this embodiment. Likewise, one or more tabs 80 are also provided as extending from the T-shaft 74 discussed above.

In order to restrain the tabs 86 in position and to engage and disengage the threads 87 of the tabs 86 with the threaded portion 60 and to thus effectively control engagement of the micro-control actuator 52 for micro-control of the sheath 20, an outer sleeve 88 can be provided, as illustrated, that slides along an outer surface of the inner sleeve 84. A compression spring 90 is also preferably provided along the outer surface of the inner sleeve 84, and is illustrated to bias the outer sleeve 88 distally. Spring 90 is shown as engaged with a proximal end 91 of the outer sleeve 88 and with an annular flange 92 that is provided at a proximal end of the inner sleeve 84. As illustrated, the flange 92 is preferably provided on a sleeve portion that is removably connected with the inner sleeve 84 (such as by way of a snap-fit) so that the compression spring 90 can be loaded to provide a bias force urging the outer sleeve 88 distally with respect to the inner sleeve 84. A distal annular flange 94 of the inner sleeve 84 provides a stop for movement of the outer sleeve 88 distally. As such, the outer sleeve 88 of this preferred embodiment of a quick release assembly to permit macro-control can move along the surface of the inner sleeve 84 under the distal bias of the spring 90. In the distal-most position of the outer sleeve 88, the tabs 86 are forced radially inward so as to be positioned radially inwardly and with the female threads 87 of the tabs 86 engaged with the male threads of the threaded portion 60 of the screw shaft 56. That is, with the outer sleeve 88 in its distal-most position, the micro-control actuator 52 is effectively engaged for micro-control of movement of the sheath 20.

The outer sleeve 88 is preferably operatively connected with the release trigger 83 so as to be movable with the trigger 83 along the range of movement that is permitted by the length of a slot 82. That way, sliding the trigger 83 proximally against the bias of the spring 90 moves the outer sleeve 88 proximally. After sufficient movement of the outer sleeve 88, the tabs 86 are released from engagement with the inner surface of the outer sleeve 88 and the tabs 86 can then move radially outward with their threaded portions 87 moved out of engagement with the threaded portion 60 of the screw shaft 56. Macro-adjustment of the sheath 20 is thus possible with the trigger moved sufficiently proximally. Release of the threaded engagement thus releases the micro-controllability by way of the micro-control actuator 52. Since the T-shaft 74 is axially fixed with the micro-control actuator 52, the degree of macro-adjustment is defined by the movement of the T-shaft 74, and in particular the one or more tabs 80, as they move along a like number of slots 64 of the threaded portion 60 of the screw shaft 56. Release of the trigger 83 allows spring 90 to move the outer sleeve 88 distally, which action moves the tabs 86 radially inwardly so that the threaded portions 87 move into engagement with the threaded portion 60 of the screw shaft 56 so as to activate micro-control of the sheath 20 by the micro-control actuator 52.

At the proximal end of the delivery system 10, a tip retractor 96 is provided that is releasably connected with the delivery system 10. Preferably, the tip retractor 96 is attached to the proximal end of the inner shaft 24 and the flush tube 38 so that when the tip retractor 96 is disconnected from the delivery system 10, as described below, the inner shaft 24, the flush tube 38 and the plunger 22 can be pulled as a unit proximally up to the point of engagement between the shoulder 26 of the nosecone 28 and the leading edge of the sheath 20. As will be more apparent with the operational description below, the greatest degree of proximal movement of the nosecone 28 to the leading edge of the sheath 20 as a result of disconnecting the tip retractor 96 will be when the micro-control actuator 52 is translated to its proximal-most position. Once the micro-control actuator 52 is rotated so that the micro-control actuator 52 is fully proximally moved, the sheath 20 assumes its fully withdrawn position relative to the plunger 22, and to a prosthetic heart valve device when supported thereon. If at this point, the trigger 83 can be moved proximally, the micro-control actuator 52 can be quickly slid along the screw shaft 56 to its distal-most position and the sheath 20 will be moved distally fully forward to cover the plunger and engage the nosecone 28. However, if the micro-control actuator 52 is positioned at a proximal-most position, or at any position that is proximal from the distal-most position of the micro-control actuator 52, the tip retractor 96 can be disconnected from the delivery system so that the plunger 22 is pulled proximally by way of the inner shaft 24 until the nosecone 28 abuts with the leading edge of the sheath 20. For example, after deployment of a prosthetic valve at a valve annulus, described more below, it may be desirable to retract the nosecone 28 and plunger 22 relative to the sheath 20 as maintained in a fixed position within the vasculature so as to avoid any movement of the sheath front edge along tissue.

In order to provide the quick disconnect between the tip retractor 96 and the remainder of the delivery system 10, an adapter 98 is provided that is connected to prevent axial movement or rotation to the proximal end of portion 62 of the screw shaft 56. The adapter 98 is preferably reduced in diameter to fit within a passage of the tip retractor and includes an annular recess 99. Spring loaded push buttons 100 are also preferably slidably supported along openings of the tip retractor 96 and biased with engagement portions 102 thereof fitted into the annular recess 99. That way, pushing both the buttons 100 inward causes a release of each of the engagement elements thereof from the annular recess 99 and thus a disconnection of the tip retractor 96 from the adapter 98, in particular, of the delivery system 10.

Also preferably incorporated within the tip retractor 96 is a flush tube hub 104. The flush hub 104 not only provides an effective one way valve and flush port (as such devices are conventionally known), but also provides an operative connection of the inner shaft 24 and the flush tube 38. With reference to FIGS. 5 and 9C, a preferred assembly of the plunger 22, inner shaft 24, flush tube 38 and flush hub 104 is described as follows. It is understood that to be operable in accordance with the present invention it is only necessary that the inner shaft 24 be able to be maintained in a position so that the outer shaft 18 is movable relative thereto, so that the plunger 22 and shield 20 are relatively movable for allowing deployment of a prosthetic valve from the plunger 22.

As shown in FIG. 5, the inner shaft 24 is preferably provided with a step at 23 leading from a distal portion at a greater diameter than a proximal portion of the inner shaft 24. The flush tube 38 can then provided to slide over the smaller diameter proximal portion of the inner shaft 24 to the point of abutment with the step 23 at one end of the flush tube 38. As shown in FIG. 9C, the proximal side of the flush tube 38 is preferably connected to the flush hub 104 at a location such as at 124. The inner shaft 24 is also preferably connected to the flush hub 104 such as at location 126. More preferably, the flush tube 38 is of an inner diameter relative to the outer diameter of the inner shaft 24 so as to create an annular lumen between these respective surface so that flush fluid can be transported distally from the flush hub 104. With the connections 124 and 126 of the flush hub to the flush tube 38 and inner tube 24, respectively, located with one distal and one proximal to the flush port of the flush hub 104, flush fluid can enter the lumen between the flush tube 38 and the inner tube 24 to flow distally from that point of the delivery system.

Referring back to FIG. 5, openings 128 through the flush tube 38 that are preferably provided near the step 23 of the inner shaft 24 allow for fluid flow from the lumen between the flush tube 38 and the inner shaft 24 by way of the openings 128. The openings 128 preferably then provide for fluid communication into a lumen that is formed between the inner shaft 24 (the greater diameter distal section thereof) and the inner diameter of the outer shaft 18 so that flush fluid can communicate all the way to the inside of the sheath 20 (see FIG. 9A). By running the outer shaft 18 further proximally that the openings 128 and preferably by closing the end of the lumen of the outer shaft 18, such as by the connection at 122 with the T-shaft 74, an effective fluid transport lumen is defined allowing for distal flow of fluid from the openings 128 and then between the outer shaft 18 and the inner shaft 24. This fluid path allows for flushing of the entire length of the delivery system through the prosthetic valve for removing air from the system. With respect to each of the connections of the stabilizing shaft 48, the outer shaft 18, the inner shaft 24 and the flush tube 38 to other components of the system, it is preferable that an adhesive bonding connection be utilized for fixing the shaft or tube ends in place. It is, however, contemplated that other bonding or securement techniques as are known or as are developed could instead be used.

Additionally, a flush hubt 106 is preferably provided at the distal end of the front grip 50 with reference to FIG. 9A. Like the flush hub 104, the flush hub 106 can be of well known and conventional construction to provide a one-way fluid access port through the hub 106. The stability shaft 48 is shown as preferably being terminated and connected distally of the hub 106, such as at location 128. A seal 130 preferably seals a lumen of the hub 106 so that fluid flows between the outer diameter surface of the outer shaft 18 and the surface of the inner diameter of the stability shaft 48 for flushing that lumen of air as well. FIG. 9A also illustrates the preferred provision of a strain relief element 110 at the distal end of the front grip 50.

Another aspect of the present invention resides within the shaping, sizing and positioning of the control handle portion 16 of the delivery system 10. Specifically, the front grip 50, micro-control actuator 52, and carriage 54 are positioned in that order going proximally from the distal end of the front grip so that when the micro-control actuator 52 is fully distally positioned, and as the carriage 54 is positioned axially adjacent to the micro-control actuator 52 by it axial connection thereto, a smooth contoured outer surface profile is created along with the front grip 50. In use, as described more below, the control handle portion 16 is typically gripped at the front grip 50 by the left hand (assuming a right handed surgeon). The surgeon's right hand is then easily positionable partially on the carriage 64 and partially on the micro-control actuator 52. The right palm would rest on the contoured surface of the carriage 54 while the right fingers could be positioned for manipulation of the micro-control actuator 52. The right thumb and first couple fingers can grasp and rotate the micro-control actuator 52 from this position, and the right thumb is positioned for easy sliding of the trigger 83 when desired.

Preferably, the front grip 50 is contoured with a curved outer surface creating an outward bulge to facilitate the surgeon's hand similar to a bicycle grip. The Carriage 54 is preferably sloped away from the micro-control actuator 52 to provide a palm rest. The micro-control actuator 52 is preferably contoured with an inward curve between outer curves, each of which outer curves tend to curve back to the level of the surface of the adjacent surfaces of the front grip 50 and the carriage 54, respectively. The inward curve provides a gripping zone for the surgeon's thumb and forefinger to affect easy rotation of the micro-control actuator 52. Overall, the profile from the leading or distal end of the control handle portion 16 to the trailing or proximal end of the control handle portion 16 is preferably a series of smooth contours including curves that facilitate easy gripping and manipulation of the control handle features, as discussed above.

An example of certain operational steps for use of a delivery system 10 of the present invention follows. The present invention is not directed to the manner of delivering or guiding a prosthetic valve to an implantation site, such as along a guide wire to the aortic valve annulus, for example, but instead is directed to manners of permitting the delivery of such a prosthetic valve at a desired site by the relative movement of the sheath 20 to a plunger 22, as such can be of any construction and having the ability to support a prosthetic valve there for deployment.

The present invention provides for the micro-control and macro-control of the movement of such plunger 22 and sheath 20 to each other from a single rotatable control member 52. Macro-control is of particular usefulness during a loading process of a prosthesis to a plunger 22, so as to allow a surgeon quick access to the plunger 22. The prosthetic valve loading process can be done in any known or developed manner onto the plunger 22. Once provided onto the plunger 22, the macro-control allows the sheath 20 to be easily positioned for holding a valve prosthesis in place. As above, macro-control is done by sliding the trigger 83 proximally for disengaging the micro-control of the micro-control actuator 52.

Once the distal tip of the delivery system is moved into place for an implantation technique, it is desirable to slowly allow a prosthetic valve to expand into position. Micro-control of movement of the sheath 20 while maintaining the plunger 22, and thus the prosthetic valve, in position to an annulus is desirable. Controlled rotation of the micro-control actuator 52 provides for such movement. After the prosthetic valve is deployed and the sheath 20 has been moved sufficiently proximally to do so, it is desirable to close the sheath 20 opening with the nosecone 28 before any further movement of the delivery system. To do this, it is preferred to utilize the disconnection of the tip retractor 96 from the screw shaft 56 so that the tip or nosecone 28 can be moved proximally to the sheath 20 while kept in place until the sheath 20 is effectively closed. Then, further system movement can be done.

An additional aspect of the present invention relates to a manner of packaging a delivery system 10 of the present invention for ease in providing all the necessary elements of the delivery system 10 to allow for storage until needed, and to facilitate quick and easy removal and set up of the delivery system with a prosthetic heart valve for use in a surgery by a surgeon at the time of the operation.

Figure 11:
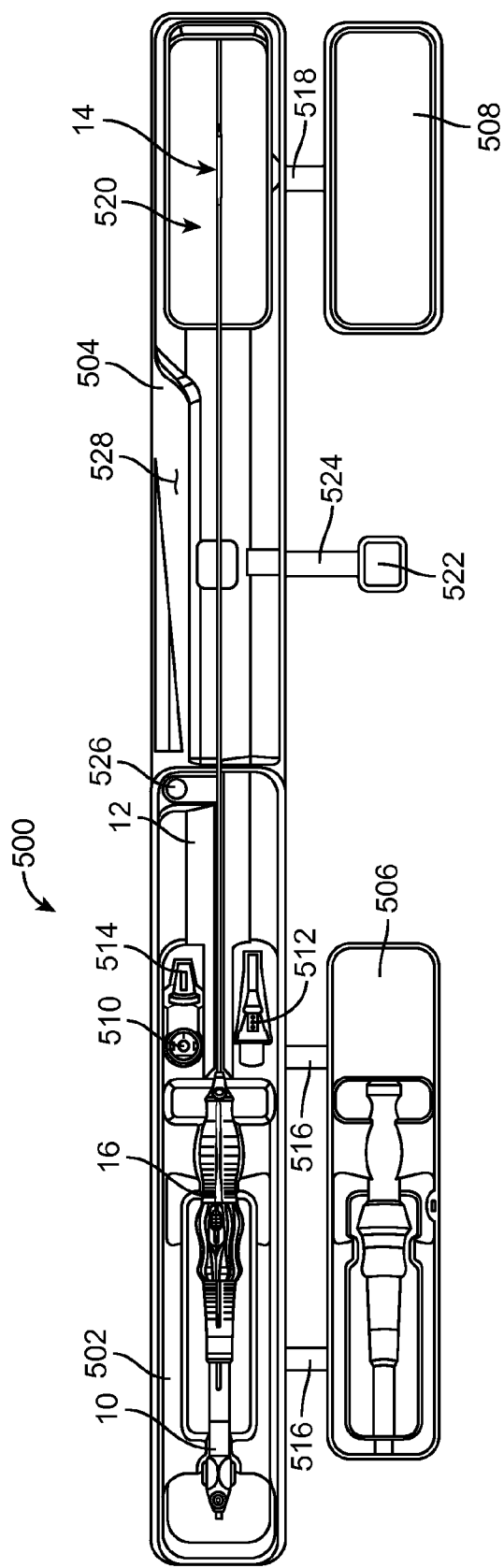
FIG. 11 is top view of a packaging and preparation tray in accordance with another aspect of the present invention including a proximal portion and a pivotal distal portion, the tray being illustrated with proximal and distal securing portions to the side of the main tray assembly and with a delivery system in accordance with the present invention also positioned within the main tray assembly.

A packaging and preparation tray assembly 500 is illustrated in FIG. 11. The packaging and preparation tray assembly 500, as illustrated, comprises a first main tray 502 for supporting a proximal portion of a delivery system 10 in accordance with the present invention and a pivotal second main tray 504 for supporting a distal portion of such a delivery system 10. The tray assembly 500 is illustrated as also including first and second securing trays 506 and 508 that are shown as positioned to the side of the first and second main trays of the tray assembly 500 and with a delivery system 10 in accordance with the present invention also positioned within the tray assembly 500.

The first main tray 502 preferably is formed to provide supporting features that are based upon the shape and dimensions of a delivery system 10 of the present invention. Preferably, the first main tray 502 is formed to support about half the length of the delivery system 10, such as including the handle control portion 16 and a part of the catheter portion 12, as such portions are described above. The second main tray 504 also preferably supports about half of the delivery system 10, such as including part of the catheter portion 12, and the deployment portion 14, as such terms are also described above.

The first and second main trays 502 and 504 are preferably formed with supports that are shaped to correspond with portions of the delivery system 10 along its length so as to keep the delivery system 10 in place as packaged. Such formed support structures are well known within plastic molding and forming technologies for packaging. As illustrated, the first main tray 502 can also include similarly formed support shapes for a prosthetic heart valve 510, such as conventionally provided within a sealed container, and a loading funnel 512 and adapter 514, as are used in the loading process of the valve 510 onto the delivery system 10, as discussed further below. The second main tray 504 is illustrated as formed to facilitate the elongate catheter portion 12 and deployment portion 14 as extended linearly from the first main tray 502. That is, the catheter portion 12 and thus the delivery system 10 can be linearly arranged without bending as packaged within the tray assembly 500 by having the first and second main trays 502 and 504 arranged end to end.

Figure 12:
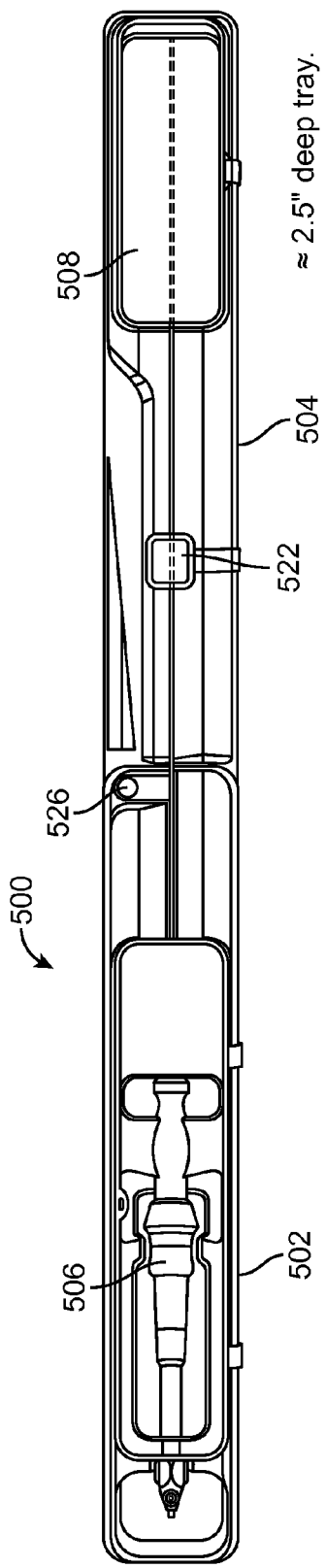
FIG. 12 is a top view similar to FIG. 11, but with the proximal and distal securing portions positioned over portions of the main tray assembly and holding a delivery system in accordance with the present invention in place.

FIG. 11 shows the tray assembly 500 with securing trays 506 and 508 not positioned over and covering portions of the delivery system 10, as such is illustrated in covered positions in FIG. 12. Securing tray 506 is shown attached to first main tray 502 by a pair of flexible hinge straps 516. These straps 516 allow the securing tray 506 to be folded over the first main tray 502 so that the securing tray 506, which is sized and formed to also fit with components of the delivery system 10, can secure the delivery system handle portion 16 with the tray assembly 500. Likewise, the securing tray 508 is movable to the second main tray 504 by one or more straps 518 (one shown) so that the securing tray can be folded over and fit against a part of the second main tray 504 for holding part of the catheter portion 12 and deployment portion 14 of the delivery system 10 in place within the tray assembly 500. Preferably, each of the securing trays 506 and 508 include edges that are sized to be tightly fitted within edges of the first and second main trays 502 and 504, respectively, as known, in order for the securing trays 506 and 508 to maintain their respective securing positions to the first and second main trays 502 and 504. Such fitting can include a snap-type fit, as known, for connected of the two, or the corresponding edges can be heat sealed, bonded, or otherwise connected to create a packaged delivery system.

With respect to the securing tray 508, in particular, a further functionality is preferably provided. That is, the securing tray 508 also can be used to effectively close a saline bath area 520 that is preferably formed into the second main tray 504 along the portion thereof that is designed to support the deployment portion 14 of the delivery system 10, at least. The bath area 520 can be formed in the second main tray 504 and can be filled with cold saline solution, as such solutions are well known for this purpose, which solution is used during a loading process of a tissue heart valve, as also described in more detail below. The second main tray 504 is also shown with a snap-fit holding element 522 that, like the securing trays 506 and 508 is attached by a strap 524 so that the holding element 522 can be folded over the second main tray 504 for securing a portion of the catheter portion 12 of the delivery system 10 in place. This feature is of particular advantage during a tissue valve loading process, as described below, for holding the catheter portion 12 in place while collapsing a metal frame tissue valve onto the plunger 22 of the deployment portion 14 of a delivery system 10 in accordance with the present invention.

FIG. 12 illustrates the first and second main trays 502 and 504 arranged end-to-end with each of the securing trays 506 and 508 positioned over and preferably snap-fit in place along with the holding feature 522. This is a preferable storage and/or shipping configuration of the tray assembly 500 of the present invention. By loading the delivery system 10 into the tray assembly in this configuration, bending of the catheter portion 12 is avoided. Conventional packages for such elongate catheter devices bend the catheter portions thereof in a U-shape, which can cause a set of a curve within the catheter tubing over time. The configuration above avoids any such concern.

Figure 13:
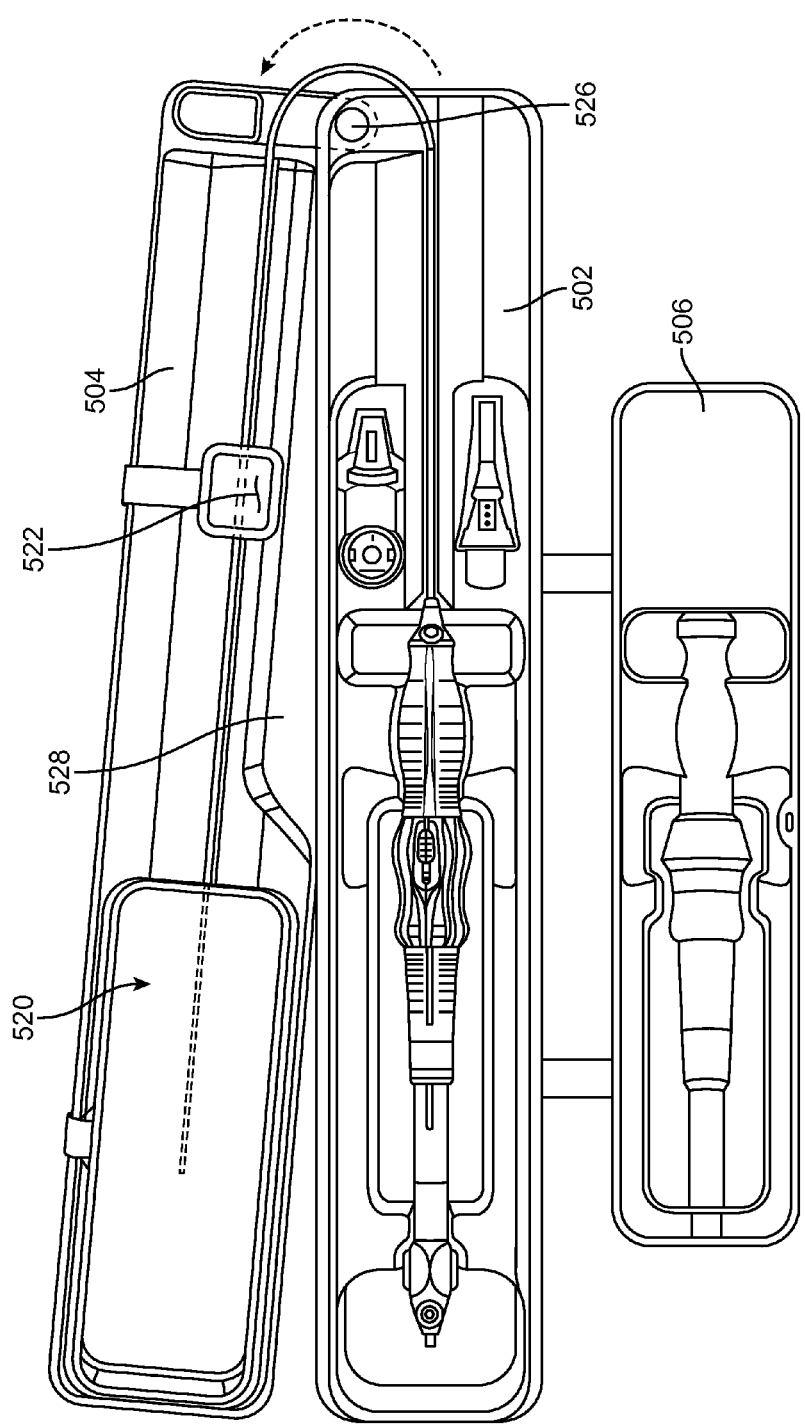
FIG. 13 is a top view of the packaging and preparation tray of FIGS. 11 and 12 but with the distal portion thereof pivoted to a position adjacent to the proximal tray portion, which position is configured to allow preparation, such as on a sterile table surface, of the delivery system and loading a prosthetic heart valve device on the distal end of the delivery system within a controlled environment, such as temperature controlled saline.

The first and second main trays 502 and 504 are also preferably operatively connected together so that they can be arranged end-to-end, as shown in FIGS. 11 and 12, and side-to-side, as illustrated in FIG. 13. To do this, a hinge 526 can be provided, as shown, that includes a pintle and bearing surface arrangement, as such can be formed into the respective corners of the first and second main trays 502 and 504. Preferably, the corresponding formed elements of such a hinge are snap-fit to keep the hinge from coming apart. To facilitate rotational movement around the hinge 526, the second main tray 504 is provided with a thin portion 528 that easily slides beneath the corner of the first main tray 502 so that a substantial side-by-side arrangement of the first and second main trays 502 and 504 can be configured by simply rotating the second main tray 504 about the hinge 526 while the first main tray 502 is stationary. Of course, either or both trays can just as easily be rotated to one another.

FIG. 13 illustrates the tray assembly in the rotated side-by-side configuration. Thin portion 528 of second main tray 504 is beneath a portion of the first main tray 502. In this configuration, the catheter portion 12 of a delivery system that is packaged within the tray assembly 500 is bent in a substantial U-shape. Moreover, the bath area 520 of the second main tray 504 is now located substantially adjacent to the proximal handle portion 16 of the delivery system. This position is advantageous for loading a tissue valve to the deployment portion 14 of the delivery system in that the elements of the handle control portion 16, as described above, can easily be manipulated while the tissue valve is prepared and loaded to the nearby deployment portion. In this regard, both micro-actuation and macro-actuation control of the sheath 20 at the distal end of such a delivery system 10 can be effected during the loading process.

Another aspect of the present invention relates to the selective surface modification of surface of a delivery system according to the present invention. It is a purpose of the utilization of such selective surface modifications to improve the force that is necessary for insertion into and through an introducer, for example, (need more info here) and to reduce tracking forces throughout a patient's vasculature, including in particular, the aortic arch for a femoral artery approach to a patient's aorta.

Preferably surface modification of select delivery system surfaces comprises the coating of such select surfaces. Other surface modifying techniques are contemplated as well that may include treatments by certain types of energy, chemical non-coating treatments, mechanical treatments, such as surface polishing, and the like. It is also contemplated to perform multiple coatings or other techniques together to one surface or selectively to distinct surfaces as effective.

Figure 14:
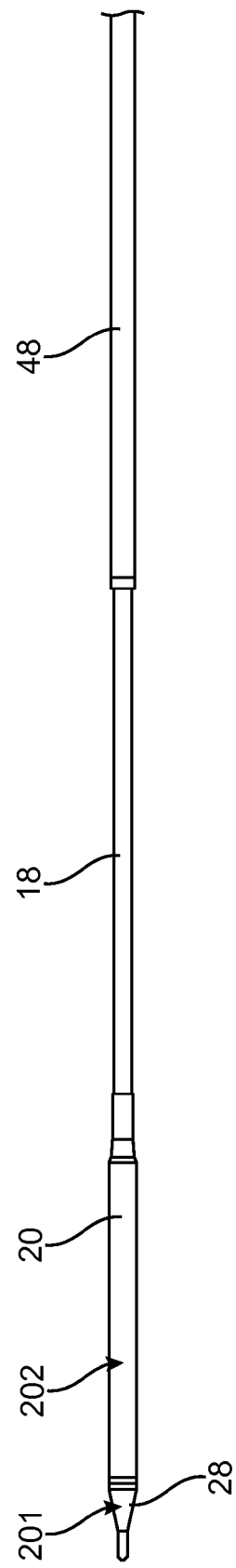
FIG. 14 is a schematic view of another aspect of the present invention including the provision of specifically coated portions of a delivery system to improve the insertion and withdrawal of the delivery system within the vasculature of a patient and for controlled deployment of a heart valve prosthesis.

In accordance with the present invention, it has been found to improve functionality of loading of a prosthetic aortic valve, for example, onto the deployment portion 14 of a delivery system 10, as illustrated in FIG. 14. In this regard, it is preferable to coat external surfaces of the delivery system nosecone 28 and the sheath 20 of a delivery system 10 with a hydrophilic coating. These portions of the delivery system 10 do not need to be contacted during the valve loading process.

Preferred coatings include those that render the polymeric material that is used for the sheath 20 and the nosecone 28 to be hydrophilic, as such coatings are commercially known and available. Preferably, the nosecone 28 comprises a soft polymeric material allowing for engagement with tissue of a vasculature system during insertion, withdrawal and manoeuvring. The sheath 20 preferably comprises a stiffer polymeric material so as to be effective in constraining an expandable prosthetic heart valve onto a plunger 22 of the delivery system, while being movable to allow expansion of the prosthetic heart valve from the plunger 22 in a controlled manner. As above, hydrophilic coatings are well known and commercially available.

In one example according to the present invention, a two-step coating process is utilized. A first coat or layer is applied to the external surface 201 of the nosecone 28 and external surface 202 of the sheath 20 followed by a top or second coating over the same surfaces. Suitable coatings includes those that are commercially available from Surmodics, Inc. of Eden Prairie, Minn., as such coatings are supplied under the trade designation as "Harmony™ Advanced Hydrophilic Coatings, specifically including the first coat PV01/K90/PR04, and the top coat PV01/K90/K30/PR04, as examples. For each coat that is applied in this example, a UV curing step is also conducted following each application step.

The invention claimed is:

1. A delivery system for percutaneous delivery of an expandable prosthetic heart valve, as such a prosthetic heart valve is to be collapsed and loaded onto a distal deployment portion of the delivery system, the delivery system comprising:

an elongate catheter portion that extends from a proximal end to a distal end and that includes a first shaft with an axial lumen and a second shaft within the lumen of the first shaft;

a deployment portion at a distal end of the delivery system that is operatively connected with the catheter portion and comprises a plunger attached to the second shaft of the catheter portion and a sheath connected with the first shaft of the catheter portion, wherein relative movement between the first and second shafts also provides relative movement between the plunger and the sheath so that a valve supporting portion of the plunger can be effectively covered and uncovered by the sheath;

a control handle portion at a proximal end of the delivery system and comprising a micro-control actuator that is operatively connected to the first shaft and is configured to advance and retract along a screw shaft that is operatively connected with the second shaft so that translation of the micro-control actuator along the screw shaft by rotation of the micro-control actuator translates the sheath relative to the plunger in a controlled micro-adjustment manner, wherein the micro-control actuator is releasable from the screw shaft so that the micro-control actuator can be translated along the screw shaft without rotation of the micro-control actuator in a controlled macro-adjustment manner; and a tip retractor disposed proximal of the control handle portion and releasably attached to the screw shaft, wherein the second shaft is connected to the tip retractor, wherein the tip retractor includes a first configuration wherein the tip retractor is attached to the screw shaft such that the second shaft does not move relative to the screw shaft and a second configuration wherein the tip retractor is released from the screw shaft such that the tip retractor, the second shaft and the plunger can be moved relative to the screw shaft.

2. The delivery system of claim 1, further comprising a front grip of the control handle portion that is fixed with the screw shaft, wherein with the tip retractor in the first configuration, the second shaft, the screw shaft, and the front grip are part of a stationary portion of the delivery system, wherein a relatively movable portion of the delivery system is movable with respect to the stationary portion, and wherein the relatively movable portion comprises the micro-control actuator and the first shaft.

3. The delivery system of claim 1, wherein the first shaft is connected to the micro-control actuator by way of a T-shaft that is movable within a passage of the screw shaft.

4. The delivery system of claim 3, wherein the screw shaft includes at least one slot along which a tab portion of the T-shaft is slidable and for limiting a range of movement of the T-shaft, and thus the first shaft and the sheath, relative to the screw shaft, and thus the second shaft and the plunger.

5. The delivery system of claim 1, further comprising a threaded insert assembly that is provided internally between the micro-control actuator and a threaded portion of the screw shaft, the threaded insert assembly comprising an inner sleeve having at least one movable element that further is provided with a threaded portion to be engagable and disengagable with the threaded portion of the screw shaft, so that when the threaded portion of the movable element of the inner sleeve is disengaged from the threaded portion of the screw shaft, macro-adjustment of the sheath to the plunger can be performed.

6. The delivery system of claim 5, further comprising an outer sleeve as part of the threaded insert assembly that is slidable relative to the inner sleeve and that is connected with a trigger, wherein in a first position of the outer sleeve relative to the inner sleeve, the threaded portion of the movable element is in threaded engagement with the threaded portion of the screw shaft for micro-adjustment.

7. The delivery system of claim 6, wherein in a second position of the outer sleeve relative to the inner sleeve, the movable element is moved such that the threaded portion of the movable element of the inner sleeve is disengaged from the threaded portion of the screw shaft for macro-adjustment.

8. The delivery system of claim 7, further comprising a spring element for biasing the outer sleeve to the first position relative to the inner sleeve.

9. A delivery system for percutaneous delivery of an expandable prosthetic heart valve, as such a prosthetic heart valve is to be collapsed and loaded onto a distal deployment portion of the delivery system, the delivery system comprising:
   an elongate catheter portion that extends from a proximal end to a distal end and that includes a first shaft with an axial lumen and a second shaft within the lumen of the first shaft;
   a deployment portion at a distal end of the delivery system that is operatively connected with the catheter portion and comprises a plunger attached to the second shaft of the catheter portion and a sheath connected with the first shaft of the catheter portion, wherein relative movement between the first and second shafts also provides relative movement between the plunger and the sheath so that a valve supporting portion of the plunger can be effectively covered and uncovered by the sheath;
   a control handle portion at a proximal end of the delivery system and comprising a micro-control actuator that is operatively connected to the sheath for moving the sheath relative to the plunger by rotation of the micro-control actuator about a screw shaft in a controlled micro-adjustment manner, wherein the micro-control actuator includes a releasable trigger for permitting linear movement of the micro-control actuator along the screw shaft and thus movement of the sheath without rotation of the micro-control actuator in a controlled macro-adjustment manner; and
   a tip retractor disposed proximal of the control handle portion and releasably attached to the screw shaft, wherein the second shaft is connected to the tip retractor, wherein the tip retractor includes a first configuration wherein the tip retractor is attached to the screw shaft such that the second shaft does not move relative to the screw shaft and a second configuration wherein the tip retractor is released from the screw shaft such that the tip retractor, the second shaft and the plunger can be moved relative to the screw shaft.

10. The delivery system of claim 9, further comprising a front grip of the control handle portion that is fixed with the screw shaft, wherein with the tip retractor in the first configuration, the second shaft, the screw shaft, the front grip and the plunger are part of a stationary portion of the delivery system, wherein a relatively movable portion of the delivery system is movable with respect to the stationary portion, and wherein the relatively movable portion comprises the micro-control actuator and the first shaft.

11. The delivery system of claim 9, wherein the first shaft is connected to the micro-control actuator by way of a T-shaft that is movable within a passage of the screw shaft.

12. The delivery system of claim 11, wherein the screw shaft includes at least one slot along which a tab portion of the T-shaft is slidable and for limiting a range of movement of the T-shaft, and thus the first shaft and the sheath, relative to the screw shaft, and thus the second shaft and the plunger.

13. The delivery system of claim 9, further comprising a threaded insert assembly that is provided internally between the micro-control actuator and a threaded portion of the screw shaft, the threaded insert assembly comprising an inner sleeve having at least one movable element that further is provided with a threaded portion to be engagable and disengagable with the threaded portion of the screw shaft, so that when the threaded portion of the movable element of the inner sleeve is disengaged from the threaded portion of the screw shaft, macro-adjustment of the sheath to the plunger can be performed.

14. The delivery system of claim 13, wherein the threaded insert assembly includes an outer sleeve that is slidable relative to the inner sleeve and that is connected with the trigger, wherein in a first position of the outer sleeve relative to the inner sleeve, the threaded portion of the movable elements is in threaded engagement with the threaded portion of the screw shaft for micro-adjustment.

15. The delivery system of claim 14, wherein in a second position of the outer sleeve relative to the inner sleeve, the movable element is moved such that the threaded portion of the movable element of the inner sleeve is disengaged from the threaded portion of the screw shaft for macro-adjustment.

16. The delivery system of claim 15, further comprising a spring element for biasing the outer sleeve to the first position relative to the inner sleeve.

17. A delivery system for percutaneous delivery of an expandable prosthetic heart valve, as such a prosthetic heart valve is to be collapsed and loaded onto a distal deployment portion of the delivery system, the delivery system comprising:
- an elongate catheter portion that extends from a proximal end to a distal end and that includes a first shaft with an axial lumen and a second shaft within the lumen of the first shaft;
- a deployment portion at a distal end of the delivery system that is operatively connected with catheter portion and comprises a plunger attached to the second shaft of the catheter portion and a sheath connected with the first shaft of the catheter portion, wherein relative movement between the first and second shafts also provides relative movement between the plunger and the sheath so that a valve supporting portion of the plunger can be effectively covered and uncovered by the sheath;
- a control handle portion at a proximal end of the delivery system and comprising a micro-control actuator that is operatively connected to the sheath for moving the sheath relative to the plunger by rotation of the micro-control actuator over a screw shaft in a controlled micro-adjustment manner, wherein a front grip is positioned distally adjacent to the micro-control actuator and a carriage is positioned proximally adjacent to the micro-control actuator, and further wherein the front grip, the micro-control actuator, and the carriage are positionable in a linear arrangement next to one another and defining a smooth contoured side profile with at least the front grip and the micro-control actuator including surface curvatures providing at least an outward bulge to the front grip and an inward curve to the micro-control actuator; and
- a tip retractor disposed proximal of the control handle portion and releasably attached to the screw shaft, wherein the second shaft is connected to the tip retractor, wherein the tip retractor includes a first configuration wherein the tip retractor is attached to the screw shaft such that the second shaft does not move relative to the screw shaft and a second configuration wherein the tip retractor is released from the screw shaft such that the tip retractor, the second shaft and the plunger can be moved relative to the screw shaft.

18. The delivery system of claim 17, wherein the front grip is fixed with the screw shaft, wherein with the tip retractor in the first configuration, the second shaft, the screw shaft, the front grip and the plunger are is thus part of a stationary portion of the delivery system, wherein a relatively movable portion of the delivery system is movable with respect to the stationary portion, and wherein the relatively movable portion comprises the micro-control actuator and the first shaft.

19. The delivery system of claim 17, wherein the first shaft is connected to the micro-control actuator by way of a T-shaft that is movable within a passage of the screw shaft.

20. The delivery system of claim 19, wherein the screw shaft includes at least one slot along which a tab portion of the T-shaft is slidable and for limiting a range of movement of the T-shaft, and thus the first shaft and the sheath, relative to the screw shaft, and thus the second shaft and the plunger.

21. The delivery system of claim 17, further comprising a threaded insert assembly that is provided internally between the micro-control actuator and a threaded portion of the screw shaft, the threaded insert assembly comprising an inner sleeve having at least one movable element that further is provided with a threaded portion to be engagable and disengagable with the threaded portion of the screw shaft, so that when the threaded portion of the movable element of the inner sleeve is disengaged from the threaded portion of the screw shaft, macro-adjustment of the sheath to the plunger can be performed.

22. The delivery system of claim 21, wherein the threaded insert assembly includes an outer sleeve that is slidable relative to the inner sleeve and that is connected with a trigger, wherein in a first position of the outer sleeve relative to the inner sleeve, the threaded portion of the movable element is in threaded engagement with the threaded portion of the screw shaft for micro-adjustment.

23. The delivery system of claim 22, wherein in a second position of the outer sleeve relative to the inner sleeve, the movable element is moved such that the threaded portion of the movable element of the inner sleeve from the threaded portion of the screw shaft for macro-adjustment.

24. The delivery system of claim 23, further comprising a spring element for biasing the outer sleeve to the first position relative to the inner sleeve.

* * * * *